US007323015B2

United States Patent
Cottard et al.

(10) Patent No.: US 7,323,015 B2
(45) Date of Patent: Jan. 29, 2008

(54) OXIDATION DYEING COMPOSITION FOR KERATIN FIBERS COMPRISING A CATIONIC POLY(VINYLLACTAM) AND AT LEAST ONE $C_{10}$-$C_{14}$ FATTY ALCOHOL, METHODS AND DEVICES FOR OXIDATION DYEING

(75) Inventors: François Cottard, Courbevoie (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/688,970

(22) Filed: Oct. 21, 2003

(65) Prior Publication Data

US 2004/0133994 A1    Jul. 15, 2004

Related U.S. Application Data

(60) Provisional application No. 60/475,495, filed on Jun. 4, 2003.

(30) Foreign Application Priority Data

Oct. 21, 2002    (FR) .................... 02 13100

(51) Int. Cl.
    *A61K 7/13*    (2006.01)
(52) U.S. Cl. .................. 8/405; 8/406; 8/407; 8/408; 8/409; 8/410; 8/412; 8/554; 8/558; 8/606; 8/611
(58) Field of Classification Search ............ 8/405, 8/406, 407, 408, 409, 410, 412, 421, 554, 8/558, 606, 611
    See application file for complete search history.

(56) References Cited

U.S. PATENT DOCUMENTS

| | | | |
|---|---|---|---|
| 2,261,002 A | 10/1941 | Ritter ..................... 260/570 |
| 2,271,378 A | 1/1942 | Searle .................... 167/22 |
| 2,273,780 A | 2/1942 | Dittmar ................... 260/28 |
| 2,375,853 A | 5/1945 | Kirby et al. .............. 260/583 |
| 2,388,614 A | 11/1945 | Kirby et al. .............. 167/23 |
| 2,454,547 A | 11/1948 | Bock et al. .............. 260/567.6 |
| 2,528,378 A | 10/1950 | Mannheimer ............ 260/309.6 |
| 2,781,354 A | 2/1957 | Mannheimer ............ 260/309.6 |
| 2,961,347 A | 11/1960 | Floyd ...................... 117/141 |
| 3,206,462 A | 9/1965 | McCarty .................. 260/256.4 |
| 3,227,615 A | 1/1966 | Korden .................... 167/87.1 |
| 3,472,840 A | 10/1969 | Stone et al. .............. 260/231 |
| 3,632,559 A | 1/1972 | Matter et al. ............. 260/78 |
| 3,836,537 A | 9/1974 | Boerwinkle et al. ....... 260/29.6 |
| 3,874,870 A | 4/1975 | Green et al. .............. 71/67 |
| 3,910,862 A | 10/1975 | Barabas et al. ............ 260/79.3 |
| 3,912,808 A | 10/1975 | Sokol ...................... 424/71 |
| 3,917,817 A | 11/1975 | Vanlerberghe et al. ...... 424/70 |
| 3,929,990 A | 12/1975 | Green et al. .............. 424/78 |
| 3,966,904 A | 6/1976 | Green et al. .............. 424/78 |
| 3,986,825 A | 10/1976 | Sokol ..................... 8/10.1 |
| 4,001,432 A | 1/1977 | Green et al. .............. 424/329 |
| 4,005,193 A | 1/1977 | Green et al. .............. 424/468 |
| 4,013,787 A | 3/1977 | Varlerberghe et al. ...... 424/70 |
| 4,025,617 A | 5/1977 | Green et al. .............. 424/78 |
| 4,025,627 A | 5/1977 | Green et al. ............ 424/248.4 |
| 4,025,653 A | 5/1977 | Green et al. .............. 424/325 |
| 4,026,945 A | 5/1977 | Green et al. ............. 260/567.6 |
| 4,027,020 A | 5/1977 | Green et al. ............ 424/248.56 |
| 4,031,307 A | 6/1977 | DeMartino et al. ........ 536/114 |
| 4,075,136 A | 2/1978 | Schaper .................... 260/2 R |
| 4,131,576 A | 12/1978 | Iovine et al. .............. 260/174 |
| 4,157,388 A | 6/1979 | Christiansen .............. 424/70 |
| 4,165,367 A | 8/1979 | Chakrabarti ............... 424/47 |
| 4,166,894 A | 9/1979 | Schaper ................... 528/271 |
| 4,172,887 A | 10/1979 | Vanlerberghe et al. ...... 424/70 |
| RE30,199 E | 1/1980 | Rose et al. ............... 8/10.2 |
| 4,189,468 A | 2/1980 | Vanlerberghe et al. ...... 424/70 |
| 4,197,865 A | 4/1980 | Jacquet et al. ............. 132/7 |
| 4,217,914 A | 8/1980 | Jacquet et al. ............. 132/7 |
| 4,223,009 A | 9/1980 | Chakrabarti ............... 424/47 |
| 4,240,450 A | 12/1980 | Grollier et al. ............. 132/7 |
| 4,277,581 A | 7/1981 | Vanlerberghe et al. ..... 525/420 |
| 4,349,532 A | 9/1982 | Vanlerberghe et al. ...... 424/47 |
| 4,422,853 A | 12/1983 | Jacquet et al. ............. 8/406 |
| 4,445,521 A | 5/1984 | Grollier et al. ............. 132/7 |
| 4,591,610 A | 5/1986 | Grollier .................... 524/55 |

(Continued)

FOREIGN PATENT DOCUMENTS

DE    23 59 399    6/1975

(Continued)

OTHER PUBLICATIONS

English language Derwent Abstract of FR 2 820 032, Aug. 2, 2002.
Co-pending U.S. Appl. No. 10/690,696, filed Oct. 21, 2003.
Co-pending U.S. Appl. No. 10/688,958, filed Oct. 21, 2003.
M.R. Porter. BSc, PhD, CChem, MRSC, "Handbook of Surfactants," Blackie & Sons Ltd., Glasgow & London, 1991, pp. 116-178.
English language Derwent Abstract of EP 0 080 976, Jun. 8, 1983.
English language abstract of JP 2-19576, Jan. 23, 1990.
English language abstract of JP 9-110659, Apr. 28, 1997.
Office Action dated Dec. 6, 2005, in co-pending U.S. Appl. No. 10/690,696.
Office Action dated May 23, 2005, in co-pending U.S. Appl. No. 10/690,696.
Office Action dated Nov. 10, 2004, in co-pending U.S. Appl. No. 10/690,696.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The disclosure relates to a composition for the oxidation dyeing of keratin fibers, for example human keratin fibers, such as hair, comprising, in an appropriate dyeing medium, at least one oxidation dye, at least one $C_{10}$-$C_{14}$ fatty alcohol and a cationic poly(vinyllactam), and to dyeing methods and devices using this composition.

59 Claims, No Drawings

U.S. PATENT DOCUMENTS

| | | | | |
|---|---|---|---|---|
| 4,608,250 A | 8/1986 | Jacquet et al. | ................ | 424/71 |
| 4,702,906 A | 10/1987 | Jacquet et al. | ................ | 424/70 |
| 4,719,099 A | 1/1988 | Grollier et al. | ............... | 424/47 |
| 4,719,282 A | 1/1988 | Nadolsky et al. | ........... | 528/310 |
| 4,761,273 A | 8/1988 | Grollier et al. | ............... | 424/47 |
| 4,803,221 A | 2/1989 | Bair | ......................... | 514/510 |
| 4,839,166 A | 6/1989 | Grollier et al. | ............... | 424/71 |
| 4,948,579 A | 8/1990 | Jacquet et al. | ................ | 424/72 |
| 4,996,059 A | 2/1991 | Grollier et al. | ............... | 424/71 |
| 5,009,880 A | 4/1991 | Grollier et al. | ............... | 424/47 |
| 5,061,289 A | 10/1991 | Clausen et al. | ................. | 8/405 |
| 5,089,252 A | 2/1992 | Grollier et al. | ............... | 424/47 |
| 5,139,037 A | 8/1992 | Grollier et al. | .............. | 132/203 |
| 5,143,518 A | 9/1992 | Madrange et al. | ............. | 8/405 |
| 5,196,189 A | 3/1993 | Jacquet et al. | ................ | 424/72 |
| 5,380,340 A | 1/1995 | Neunhoeffer et al. | .......... | 8/409 |
| 5,534,267 A | 7/1996 | Neunhoeffer et al. | ....... | 424/701 |
| 5,587,155 A | 12/1996 | Ochiai et al. | | |
| 5,663,366 A | 9/1997 | Neunhoeffer et al. | .... | 548/371.4 |
| 5,766,576 A | 6/1998 | Löwe et al. | ................. | 424/62 |
| 5,868,800 A | 2/1999 | Cotteret et al. | ................ | 8/410 |
| 5,958,392 A | 9/1999 | Grollier et al. | .......... | 424/70.17 |
| 6,099,592 A | 8/2000 | Vidal et al. | .................... | 8/409 |
| 6,099,593 A | 8/2000 | Terranova et al. | ............. | 8/409 |
| 6,284,003 B1 | 9/2001 | Rose et al. | .................... | 8/412 |
| 6,338,741 B1 | 1/2002 | Vidal et al. | .................... | 8/409 |
| 6,645,258 B2 | 11/2003 | Vidal et al. | .................... | 8/405 |
| 2001/0023514 A1* | 9/2001 | Cottard et al. | ................ | 8/406 |
| 2002/0046431 A1 | 4/2002 | Laurent et al. | ................ | 8/405 |
| 2002/0050013 A1 | 5/2002 | Vidal et al. | .................... | 8/405 |
| 2003/0019051 A9 | 1/2003 | Vidal et al. | .................... | 8/405 |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 080 976 | 6/1983 |
| EP | 01 122 324 A1 | 10/1984 |
| EP | 0 337 354 A1 | 10/1989 |
| EP | 1 179 336 | 2/2002 |
| EP | 1 321 134 | 6/2003 |
| FR | 1 400 366 | 4/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 750 048 | 12/1997 |
| FR | 2 820 032 | 8/2002 |
| GB | 1 021 400 | 3/1966 |
| GB | 1 026 978 | 4/1966 |
| GB | 1 153 196 | 5/1969 |
| GB | 1 546 809 | 5/1979 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 00/67282 | 11/2000 |

OTHER PUBLICATIONS

Office Action dated Jul. 5, 2005, in co-pending U.S. Appl. No. 10/688,958.

Office Action dated Nov. 9, 2004, in co-pending U.S. Appl. No. 10/688,958.

* cited by examiner

OXIDATION DYEING COMPOSITION FOR KERATIN FIBERS COMPRISING A CATIONIC POLY(VINYLLACTAM) AND AT LEAST ONE $C_{10}$-$C_{14}$ FATTY ALCOHOL, METHODS AND DEVICES FOR OXIDATION DYEING

This application claims benefit of U.S. Provisional Application No. 60/475,495, filed Jun. 4, 2003.

Disclosed herein is a composition for the oxidation dyeing of keratin fibers, for example, human keratin fibers such as hair, comprising at least one oxidation dye, at least one cationic poly(vinyllactam) and at least one particular fatty alcohol.

It is known to dye keratin fibers, such as human hair, with dyeing compositions containing oxidation dye precursors, generally called "oxidation bases," for instance ortho- or para-phenylenediamines, ortho- or para-aminophenols, and heterocyclic bases.

Oxidation dye precursors are compounds initially only slightly colored or not colored, which develop their dyeing power in the hair in the presence of oxidizing agents, leading to the formation of colored compounds. The formation of these colored compounds can result either from oxidative condensation of the "oxidation bases" with themselves, or oxidative condensation of the "oxidation bases" with color modifying compounds, or "couplers", which are generally present in the dyeing compositions used in oxidation dyeing and are represented for instance by meta-phenylenediamines, meta-aminophenols and meta-diphenols, and certain heterocyclic compounds.

The variety of molecules used, which include, on the one hand, "oxidation bases" and on the other hand, "couplers," allows a very rich palette of colors to be obtained.

To confine the oxidation dyeing product upon application to the hair so that it does not run over the face or outside the areas which it is desired to dye, use has up until now been made of traditional thickeners such as crosslinked polyacrylic acid, hydroxyethyl-celluloses, certain polyurethanes, waxes or mixtures of nonionic surfactants having an HLB (Hydrophilic Lipophilic Balance), suitably chosen, which produce a gelling effect when they are diluted with water and/or surfactants.

Most of the thickening systems of the prior art may not make it possible to obtain intense and chromatic shades of low selectivity and good fastness and to offer a good cosmetic condition to the treated hair. Moreover, it has been observed that most of the ready-to-use dyeing compositions of the prior art containing at least one oxidation dye, and a thickening system may not allow a sufficiently precise application without running or drops in viscosity over time.

French Patent Application FR 2 820 032 describes ready-to-use oxidation dyeing compositions which do not run and therefore remain well confined to the site of application. These compositions comprise, in an appropriate dyeing medium, at least one oxidation dye, and at least one cationic poly(vinyllactam); they also make it possible to obtain intense and chromatic (radiant) shades with low selectivities and good fastness towards chemical agents (shampoo, permanent waving and the like) or natural agents (light, perspiration and the like) while offering the hair good cosmetic properties.

The compositions comprising at least one oxidation dye and a thickening system may be provided in the form of creams. The current technology in the oxidation dye field usually requires that these compositions, in order to acquire a cream appearance, comprise high contents of fatty active agents (alcohols, amides, acids).

However, the present inventors have observed that as the viscosity of these creams changes during their preservation or storage; it is difficult to obtain a homogeneous mixture when these compositions are mixed in the form of a cream with an oxidizing agent. In addition, the consistency of these creams makes them difficult to use.

Advantageously and surprisingly, the present inventors have discovered that it was possible to obtain ready-to-use oxidation dyeing compositions that can exhibit an increased ease of mixing with the oxidizing agent and the other optional components, an improvement in the foaming properties and an increased ease of elimination, such as during rinsing.

In addition, these compositions as disclosed herein do not run and therefore remain well confined to the site of application. They also make it possible to obtain intense and chromatic (radiant) shades with low selectivity and good fastness towards chemical agents (shampoo, permanent waving and the like) or natural agents (light, perspiration and the like) while offering the hair good cosmetic properties.

It has also been observed that the compositions according to the invention can have reduced contents of fatty active agents compared with the contents of prior art compositions without the consistency of the composition (cream) being affected.

One subject of the present disclosure is thus a composition for the oxidation dyeing of keratin fibers, such as human keratin fibers, for instance, hair, comprising, in an appropriate dyeing medium, at least one oxidation dye, at least one $C_{10}$-$C_{14}$ fatty alcohol and at least one cationic poly(vinyllactam).

Another subject of the disclosure relates to a ready-to-use composition for dyeing keratin fibers which contains at least one oxidation dye, at least one $C_{10}$-$C_{14}$ fatty alcohol and at least one cationic poly(vinyllactam) as defined below and an oxidizing agent.

The expression "ready-to-use composition" is understood to mean, for the purposes of the invention, the composition intended to be applied as it is to keratin fibers. That is to say, the composition can be stored as it is before use or be obtained from the fresh mixing of two or more compositions.

An effective quantity of cationic poly(vinyllactam) may be introduced:
  (i) either into the composition comprising the at least one oxidation dye and optionally the at least one coupler (composition A),
  (ii) or into the oxidizing composition (composition B), or
  (iii) into both compositions at the same time.

An effective quantity of $C_{10}$-$C_{14}$ fatty alcohol may be introduced
  (i) either into the composition containing the at least one oxidation dye and optionally the at least one coupler (composition A),
  (ii) or into the oxidizing composition (composition B), or
  (iii) into both compositions at the same time.

For example, the $C_{10}$-$C_{14}$ fatty alcohol may be introduced into the composition comprising the oxidation dye(s).

Also disclosed herein is a method for dyeing keratin fibers, for example human keratin fibers such as hair, comprising applying to the fibers at least one composition A comprising, in an appropriate dyeing medium, at least one oxidation dye, the color being developed at alkaline, neutral or acidic pH with the aid of a composition B comprising at least one oxidizing agent which is mixed just at the time of use with the composition A or which is applied sequentially without intermediate rinsing, at least one cationic poly(vinyllactam) as defined below being present in the composition A or in the composition B or in each of the compositions A and B, and at least one $C_{10}$-$C_{14}$ fatty alcohol as defined below being present in the composition A or in the composition B or in each of the compositions A and B.

Further disclosed herein are multicompartment dyeing devices or "kits".

A 2-compartment device, as disclosed herein, may comprise a compartment comprising a composition A1 comprising, in an appropriate dyeing medium, at least one oxidation dye, and another compartment comprising a composition B1 comprising, in an appropriate dyeing medium, an oxidizing agent, wherein the cationic poly(vinyllactam) polymer as defined below may be present in the composition A1 or the composition B1, or in each of the compositions A1 and B1 and wherein the $C_{10}$-$C_{14}$ fatty alcohol as defined below may be present in the composition A1 or the composition B1, or in each of the compositions A1 and B1.

Another device, with 3 compartments, comprises a first compartment comprising a composition A2 comprising, in an appropriate dyeing medium, at least one oxidation dye, a second compartment comprising a composition B2 containing, in an appropriate dyeing medium, at least one oxidizing agent, and a third compartment comprising a composition C comprising, in an appropriate dyeing medium, at least one cationic poly(vinyllactam) polymer, it being also possible for the composition A2 and/or the composition B2 to comprise a cationic poly(vinyllactam) polymer as defined below and it being also possible for the composition A2 and/or the composition B2 and/or the composition C to comprise a $C_{10}$-$C_{14}$ fatty alcohol as defined below.

Other characteristics, aspects, subjects and advantages of the disclosure will appear more clearly on reading the description and the examples which follow.

Associative polymers are polymers whose molecules are capable, in the formulation medium, of combining with each other or with molecules of other compounds.

Their chemical structure generally comprises at least one hydrophilic region and at least one hydrophobic region, the hydrophobic region(s) comprising at least one fatty chain.

Cationic Polyvinyllactam Polymers According to the Invention

The cationic poly(vinyllactam) polymers used herein comprise:
a) at least one monomer of the vinyllactam or alkylvinyllactam type; and
b) at least one monomer chosen from monomers having structures (Ia) or (Ib):

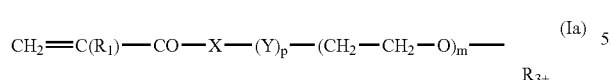

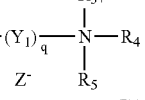

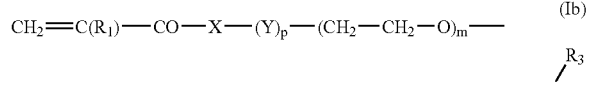

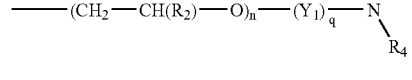

wherein:
X is chosen from an oxygen atom and $NR_6$ radicals,
$R_1$ and $R_6$, which may be identical or different, are chosen from hydrogen atoms, and linear and branched $C_1$-$C_5$ alkyl radicals,
$R_2$ is chosen from linear and branched $C_1$-$C_4$ alkyl radicals,
$R_3$, $R_4$ and $R_5$, which may be identical or different, are chosen from hydrogen atoms, linear and branched $C_1$-$C_{30}$ alkyl radicals, and radicals of formula (II):

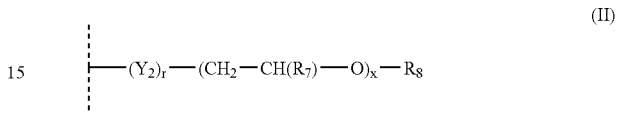

wherein
Y, $Y_1$ and $Y_2$, which may be identical or different, are chosen from linear and branched $C_2$-$C_{16}$ alkylene radicals,
$R_7$ is chosen from hydrogen atoms, linear and branched $C_1$-$C_4$ alkyl radicals, and linear and branched $C_1$-$C_4$ hydroxyalkyl radicals,
$R_8$ is chosen from hydrogen atoms, linear and branched $C_1$-$C_{30}$ alkyl radicals,
p, q and r, which may be identical or different, are integers chosen from zero and 1,
m and n, which may be identical or different, are integers ranging from 0 to 100,
x is an integer ranging from 1 to 100,
Z is chosen from organic and inorganic acid anions,
provided that:
at least one of the substituents $R_3$, $R_4$, $R_5$ and $R_8$ is chosen from linear and branched $C_9$-$C_{30}$ alkyl radicals,
if m or n is different from zero, then q is equal to 1, and
if m or n are equal to zero, then p or q is equal to 0.

The cationic poly(vinyllactam) polymers used herein may be chosen from crosslinked and noncrosslinked polymers and may also be block polymers.

For example, the counterion $Z^-$ of the monomers of formula (Ia) may be chosen from halide ions, phosphate ions, methosulphate ions, and tosylate ions.

For instance, $R_3$, $R_4$ and $R_5$, which may be identical or different, may be chosen from hydrogen atoms, linear and branched $C_1$-$C_{30}$ alkyl radicals.

As another example, the monomer b) may be a monomer of formula (Ia) wherein m and n are equal to zero.

In one instance, the vinyllactam or alkylvinyllactam monomer may be a compound having the structure (III):

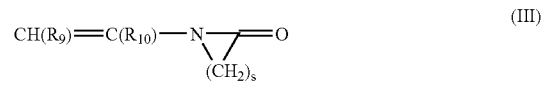

wherein:
s is an integer ranging from 3 to 6,
$R_9$ is chosen from hydrogen atoms and $C_1$-$C_5$ alkyl radicals,
$R_{10}$ is chosen from hydrogen atoms and $C_1$-$C_5$ alkyl radicals,
provided that at least one of the radicals $R_9$ and $R_{10}$ is a hydrogen atom.

For instance, the monomer (III) may be vinylpyrrolidone.

The cationic poly(vinyllactam) polymers used herein may also comprise at least one additional monomer, chosen, for example, from cationic and non-ionic monomers.

As non-limiting examples of compounds which may be used herein, there may be mentioned terpolymers comprising at least:

a) one monomer of formula (III), b) one monomer of formula (Ia) wherein p=1, q=0, $R_3$ and $R_4$, which may be identical or different, are chosen from hydrogen atoms and $C_1$-$C_5$ alkyl radicals, and $R_5$ is chosen from $C_9$-$C_{24}$ alkyl radicals, and c) one monomer of formula (Ib) wherein $R_3$ and $R_4$, which may be identical or different, may be chosen from hydrogen atoms and $C_1$-$C_5$ alkyl radicals.

For example, the monomers may be used in the terpolymers in amounts comprising, by weight, 40 to 95% of monomer (a), 0.1 to 55% of monomer (c) and 0.25 to 50% of monomer (b).

Such polymers are described in patent application WO-00/68282, the disclosure of which is hereby incorporated by reference.

As cationic poly(vinyllactam) polymers useful herein, there may be used for instance, terpolymers chosen from the following:

vinylpyrrolidone/dimethylaminopropylmethacrylamide/dodecyldimethylmethacrylamidopropylammonium tosylate, vinylpyrrolidone/dimethylaminopropylmethacrylamide/cocoyldimethylmethacrylamidopropylammonium tosylate, vinylpyrrolidone/dimethylaminopropylmethacrylamide/lauryldimethylmethacrylamidopropylammonium tosylate, and vinylpyrrolidone/dimethylaminopropylmethacrylamide/lauryldimethylmethacrylamidopropylammonium chloride.

The weight-average molecular mass of the cationic poly(vinyllactam) polymers according to the present disclosure may range from 500 to 20 000 000. For further example, the weight-average molecular mass may range from 200 000 to 2 000 000, such as from 400 000 to 800 000.

In the dyeing composition(s) according to the present disclosure, the cationic poly(vinyllactam) or poly(vinyllactams) described above may be used in a quantity which may vary from about 0.01 to 10% by weight, relative to the total weight of the composition. For example, this quantity may vary from about 0.1 to 5% by weight.

As an example, the viscosity of the compositions according to the disclosure may be greater than 1 000 cp, measured at 25° C. using a RHEOMAT RM 180 rheometer at the shear rate of 200 s$^{-1}$.

$C_{10}$-$C_{14}$ Fatty Alcohols

The fatty alcohols used in the composition disclosed herein are $C_{10}$-$C_{14}$ fatty alcohols. They may be nonpolyoxyalkylenated or polyoxyalkylenated. In one embodiment, the fatty alcohols may be polyoxyalkylenated. The polyoxyalkylenated fatty alcohols may comprise from 2 to 20 oxyethylene (EO) units, such as from 3 to 15 oxyethylene (EO) units.

For example, the polyoxyalkylenated fatty alcohols may be chosen from capryl, lauryl and myristyl alcohols, and mixtures thereof. For example, oxyethylenated (12 EO) lauryl alcohol and/or oxyethylenated (3 EO) decyl alcohol may be used.

In the dyeing composition disclosed herein, the $C_{10}$-$C_{14}$ fatty alcohol(s) may be used in a quantity which may vary from about 0.1% to 40% by weight of the total weight of the composition, for example from about 2% to 25%, such as from 5% to 20%.

Oxidation Dyes

The at least one oxidation dye which can be used herein is chosen from at least one oxidation base and at least one oxidation coupler.

For instance, the compositions disclosed herein may contain at least one oxidation base. The oxidation bases which can be used are chosen from those conventionally known in oxidation dyeing, and among which there may be mentioned para-phenylenediamines, double bases, ortho- and para-aminophenols, the following heterocyclic bases as well as their acid addition salts.

There may be mentioned, for example:

(A) the para-phenylenediamines of the following formula (IV) and their acid addition salts:

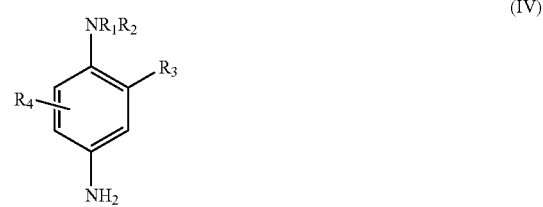

in which:

$R_1$ is chosen from a hydrogen atom, $C_1$-$C_4$ alkyl radicals, monohydroxy($C_1$-$C_4$ alkyl) radicals, polyhydroxy($C_2$-$C_4$ alkyl) radicals, ($C_1$-$C_4$)alkoxy($C_1$-$C_4$)alkyl radicals, $C_1$-$C_4$ alkyl radicals substituted with a nitrogen-containing group, phenyl radicals and 4'-aminophenyl radicals;

$R_2$ is chosen from a hydrogen atom, $C_1$-$C_4$ alkyl radicals, monohydroxy($C_1$-$C_4$ alkyl) radicals, polyhydroxy($C_2$-$C_4$ alkyl) radicals, ($C_1$-$C_4$)alkoxy($C_1$-$C_4$)alkyl radicals, and $C_1$-$C_4$ alkyl radicals substituted with a nitrogen-containing group;

$R_1$ and $R_2$ may also form, with the nitrogen atom carrying them, a 5- or 6-membered nitrogen-containing heterocycle optionally substituted with at least one group chosen from alkyl, hydroxyl and ureido groups;

$R_3$ is chosen from a hydrogen atom, halogen atoms, such as a chlorine atom, $C_1$-$C_4$ alkyl radicals, sulpho radicals, carboxyl radicals, monohydroxy($C_1$-$C_4$ alkyl) radicals, hydroxy($C_1$-$C_4$ alkoxy) radicals, acetylamino($C_1$-$C_4$ alkoxy) radicals, mesylamino($C_1$-$C_4$ alkoxy) radicals, and carbamoylamino($C_1$-$C_4$ alkoxy) radicals, $R_4$ is chosen from a hydrogen atom, halogen atoms, and $C_1$-$C_4$ alkyl radicals.

Among the nitrogen-containing groups of formula (IV) above, there may be mentioned, for example, the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the para-phenylenediamines of formula (IV) above, there may be mentioned, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and the acid addition salts thereof.

Among the para-phenylenediamines of formula (IV) above, as a further example, there may be mentioned para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and the acid addition salts thereof.

(B) According to the invention, "double bases" is understood to mean the compounds containing at least two aromatic rings on which amino and/or hydroxyl groups are carried.

Among the double bases which can be used as oxidation bases in the dyeing compositions disclosed herein, there may be mentioned, for example, the compounds corresponding to the following formula (V), and the acid addition salts thereof:

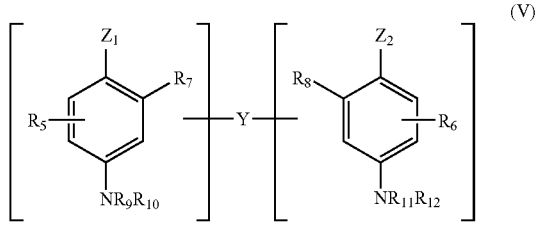

in which:
$Z_1$ and $Z_2$, which may be identical or different, are chosen from hydroxyl radicals, and with —$NH_2$ radicals which may be substituted with a $C_1$-$C_4$ alkyl radical or with a linking arm Y;
the linking arm Y is chosen from linear and branched alkylene chains comprising from 1 to 14 carbon atoms, which may be interrupted by or which may end with at least one nitrogen-containing group and/or at least one heteroatom such as oxygen, sulphur or nitrogen atoms, and is optionally substituted with at least one radical chosen from hydroxyl and $C_1$-$C_6$ alkoxy radicals;
$R_5$ and $R_6$ are chosen from a hydrogen atom, halogen atoms, $C_1$-$C_4$ alkyl radicals, monohydroxy($C_1$-$C_4$ alkyl) radicals, polyhydroxy($C_2$-$C_4$ alkyl) radicals, amino($C_1$-$C_4$ alkyl) radicals, and a linking arm Y;
$R_7$, $R_8$, $R_9$, $R_{10}$, $R_{11}$ and $R_{12}$, which may be identical or different, are chosen from a hydrogen atom, a linking arm Y and $C_1$-$C_4$ alkyl radicals;
with the proviso that the compounds of formula (V) contain only one linking arm Y per molecule.

Among the nitrogen-containing groups of formula (V) above, there may be mentioned, for example, the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the double bases of formulae (V) above, there may be mentioned, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis-(4-aminophenyl)tetramethylenediamine, N,N'-bis(4-methylaminophenyl) tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Among these double bases of formula (V), as further examples may be mentioned N,N'-bis(β-hydroxyethyl)-N,N'-bis(4'-aminophenyl)-1,3-diaminopropanol, 1,8-bis(2,5-diaminophenoxy)-3,6-dioxaoctane and the acid addition salts thereof.

(C) the para-aminophenols corresponding to the following formula (VI), and their acid addition salts:

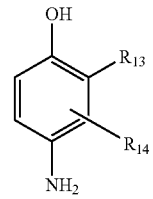

in which:
$R_{13}$ is chosen from a hydrogen atom, halogen atoms, such as fluorine, and $C_1$-$C_4$ alkyl, monohydroxy($C_1$-$C_4$ alkyl), ($C_1$-$C_4$)alkoxy($C_1$-$C_4$)alkyl, amino($C_1$-$C_4$ alkyl), and hydroxy($C_1$-$C_4$)alkylamino($C_1$-$C_4$ alkyl) radicals,
$R_{14}$ is chosen from a hydrogen atom, halogen atoms, such as fluorine, and $C_1$-$C_4$ alkyl, monohydroxy($C_1$-$C_4$ alkyl), polyhydroxy($C_2$-$C_4$ alkyl), amino($C_1$-$C_4$ alkyl), cyano($C_1$-$C_4$ alkyl), and ($C_1$-$C_4$)alkoxy($C_1$-$C_4$)alkyl radicals.

Among the para-aminophenols of formula (VI) above, there may be mentioned, for instance, para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their acid addition salts.

(D) the ortho-aminophenols which can be used as oxidation bases herein may be chosen from 2-aminophenol, 2-amino-1-hydroxy-5-methylbenzene, 2-amino-1-hydroxy-6-methylbenzene, 5-acetamido-2-aminophenol, and their acid addition salts.

(E) among the heterocyclic bases which can be used as oxidation bases in the dyeing compositions in accordance with the invention, there may be mentioned, for example, pyridine derivatives, pyrimidine derivatives, pyrazole derivatives, and their acid addition salts.

Among the pyridine derivatives, there may be mentioned the compounds described for example in Patents GB 1,026,978 and GB 1,153,196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine, and their acid addition salts.

Among the pyrimidine derivatives, there may be mentioned the compounds described for example in German Patent DE 2,359,399 or Japanese Patents JP 88-169,571 and JP 91-10659 or Patent Applications WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; and their addition salts and their tautomeric forms, when a tautomeric equilibrium exists.

Among the pyrazole derivatives, there may be mentioned, for example, the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methyl pyrazole, and the acid addition salts thereof.

In the compositions disclosed herein, the at least one oxidation base may be present in an amount ranging from 0.0005 to 20% by weight relative to the total weight of the composition, such as from 0.005 to 8% by weight.

The at least one coupler useful in the dyeing method disclosed herein may be chosen from those conventionally used in oxidation dyeing compositions, such as meta-aminophenols, meta-phenylenediamines, meta-diphenols, naphthols and heterocyclic couplers such as for example indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and the acid addition salts thereof.

The at least one coupler may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole and the acid addition salts thereof.

When they are present, the coupler(s) may be present in the composition in an amount ranging from 0.0001 to 20% by weight relative to the total weight of the composition, such as from 0.005 to 5% by weight.

In general, the acid addition salts of the oxidation bases and couplers may be chosen from hydrochlorides, hydrobromides, sulphates, tartrates, lactates and acetates.

The composition disclosed herein may also contain, in addition to the oxidation dyes defined above, at least one direct dye in order to enrich the shades with glints. These direct dyes may be chosen from neutral, cationic and anionic nitro, azo and anthraquinone dyes in an amount by weight of about 0.001 to 20%, such as from 0.01 to 10% relative to the total weight of the composition.

The composition A and/or the composition B and/or the composition C may in addition contain at least one additional polymer chosen from at least one amphoteric polymer and at least one cationic polymer different from the cationic poly(vinyllactams) disclosed herein.

Cationic Polymers Different from the Disclosed Cationic Poly(vinyllactams)

As used herein, the expression "cationic polymer" denotes any polymer containing cationic groups and/or groups which can be ionized to cationic groups.

The at least one cationic polymer which can be used herein may be chosen from all those already known per se to improve the cosmetic properties of hair, such as those described in Patent Application EP-A-337 354 and in French patents FR-2,270,846, 2,383,660, 2,598,611, 2,470,596 and 2,519,863.

For example, the at least one cationic polymer may be chosen from those cationic polymers which contain units comprising primary, secondary, tertiary and/or quaternary amino groups which may either form part of the principal polymeric chain, or which may be carried by a side substituent directly linked thereto.

The at least one cationic polymer used herein generally has a number-average molecular mass ranging from 500 to $5 \times 10^6$, such as from $10^3$ to $3 \times 10^6$.

Among the cationic polymers, there may be mentioned, for example, the polymers of the polyamine, polyamino amide and quaternary polyammonium type. These are known products, described, for example, in French Patent No. 2,505,348 and 2,542,997. Among these polymers, there may be mentioned:

(1) the homopolymers or copolymers derived from acrylic or methacrylic esters or amides and comprising at least one of the units of the following formulae (VII), (VIII), (IX) or (X):

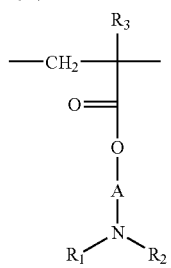

(VII)

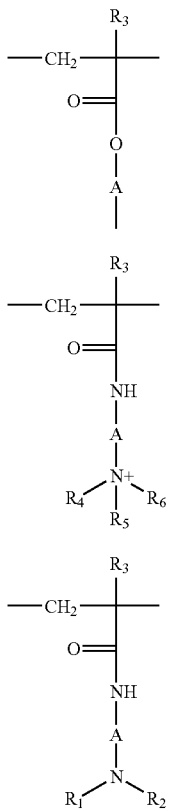

in which:

R$_3$, which may be identical or different, are chosen from a hydrogen atom and a CH$_3$ radical;

A, which may be identical or different, are chosen from linear and branched alkyl groups having 1 to 6 carbon atoms, such as 2 or 3 carbon atoms, and from hydroxyalkyl groups having 1 to 4 carbon atoms;

R$_4$, R$_5$, R$_6$, which may be identical or different, are chosen from alkyl groups having from 1 to 18 carbon atoms, such as from 1 to 6 carbon atoms, and from benzyl radicals;

R$_1$ and R$_2$, which may be identical or different, are chosen from hydrogen and alkyl groups having from 1 to 6 carbon atoms, such as methyl and ethyl groups;

the charged species (VIII) and (IX) are combined with a counterion X$^-$, wherein X$^-$ is chosen from anions derived from an inorganic or organic acid such as a methosulphate anion and from halides such as chloride or bromide.

The polymers of the family (1) may contain, in addition, at least one unit derived from comonomers which may be chosen from the family of acrylamides, methacrylamides, diacetone acrylamides, acrylamides and methacrylamides substituted on the nitrogen with lower (C$_1$-C$_4$)alkyls, acrylic or methacrylic acids or esters thereof, vinyllactams such as vinylpyrrolidone or vinylcaprolactam, and vinyl esters.

Thus, among these polymers of the family (1), there may be mentioned:

the copolymers of acrylamide and dimethylamino-ethyl methacrylate quaternized with dimethyl sulphate or with a dimethyl halide such as that sold under the name HERCOFLOC® by the company HERCULES, the copolymers of acrylamide and methacryloyloxyethyltrimethylammonium chloride described, for example, in Patent Application EP-A-080976 and sold under the name BINA QUAT P 100® by the company CIBA GEIGY, the copolymer of acrylamide and methacryloyloxyethyltrimethylammonium methosulphate sold under the name RETEN® by the company HERCULES, the vinylpyrrolidone/dialkylaminoalkyl acrylate or methacrylate copolymers, quaternized or otherwise, such as the products sold under the name "GAFQUAT®" by the company ISP such as for example "GAFQUAT 734" or "GAFQUAT 755" or alternatively the products called "COPOLYMER 845®, 958® and 937®". These polymers are described in detail in French Patents 2,077,143 and 2,393,573, the dimethylaminoethyl methacrylate/vinylcaprolactam/vinylpyrrolidone terpolymers such as the product sold under the name GAFFIX VC 713® by the company ISP, the vinylpyrrolidone/methacrylamidopropyldimethylamine copolymers marketed in particular under the name STYLEZE CC 10® by ISP, and the quaternized vinylpyrrolidone/dimethyl-aminopropyl methacrylamide copolymers such as the product sold under the name "GAFQUAT® HS 100" by the company ISP.

(2) The cellulose ether derivatives comprising quaternary ammonium groups, described in French Patent 1,492,597, for example, the polymers marketed under the names "JR®" (JR 400, JR 125, JR 30M) or "LR®" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described for instance in U.S. Pat. No. 4,131,576, such as hydroxyalkyl celluloses like hydroxymethyl, hydroxyethyl or hydroxypropyl celluloses grafted with a methacryloylethyltrimethylammonium, methacrylamidopropyltrimethylammonium or dimethyldiallylammonium salt.

The commercialized products corresponding to this definition are, for example, the products sold under the name "Celquat® L 200" and "Celquat® H 100" by the company National Starch.

(4) The cationic polysaccharides described more particularly in U.S. Pat. Nos. 3,589,578 and 4,031,307 such as guar gums containing cationic trialkylammonium groups. Guar gums modified with a 2,3-epoxypropyltrimethylammonium salt (e.g. chloride) are for example used.

Such products are marketed, for example, under the trade names JAGUAR® C13 S, JAGUAR® C15, JAGUAR® C17 or JAGUAR® C162 by the company MEYHALL.

(5) Polymers consisting of piperazinyl units and of alkylene or hydroxyalkylene divalent radicals with straight or branched chains, optionally interrupted by oxygen, sulphur or nitrogen atoms or by aromatic or heterocyclic rings, as well as the oxidation and/or quaternization products of these polymers. Such polymers are described especially in French Patent Nos. 2,162,025 and 2,280, 361.

(6) Water-soluble polyaminoamides prepared, for example, by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive towards a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described, for example, in French Patent Nos. 2,252,840 and 2,368,508.

(7) Polyaminoamide derivatives resulting from the condensation of polyalkylenepolyamines with polycarboxylic acids, followed by an alkylation with difunctional agents. There may be mentioned, for example, the adipic acid—dialkylaminohydroxyalkyl-dialkylenetriamine polymers in which the alkyl radical contains from 1 to 4 carbon atoms and further may be chosen from methyl, ethyl and propyl. Such polymers are described, for example, in French Patent 1,583,363.

Among these derivatives there may be mentioned the adipic acid/dimethylaminohydroxypropyl/diethylenetriamine polymers sold under the name "Cartaretine® F, F4 or F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid ranges from 0.8:1 to 1.4:1; the polyaminoamide resulting therefrom being made to react with epichlorohydrin in a molar ratio of epichlorohydrin relative to the secondary amine group of the polyaminoamide of from 0.5:1 to 1.8:1. Such polymers are described, for example, in U.S. Pat. Nos. 3,227,615 and 2,961,347.

Polymers of this type are marketed, for example, under the name "Hercosett® 57" by the company Hercules Inc. or else under the name of "PD 170®" or "Delsette 101®" by the company Hercules in the case of the copolymer of adipic acid/epoxypropyl/diethylene-triamine.

(9) Cyclopolymers of alkyldiallylamine or of dialkyldiallylammonium, such as the homopolymers or copolymers comprising, as main constituent of the chain, units corresponding to the formulae (XI) or (XII):

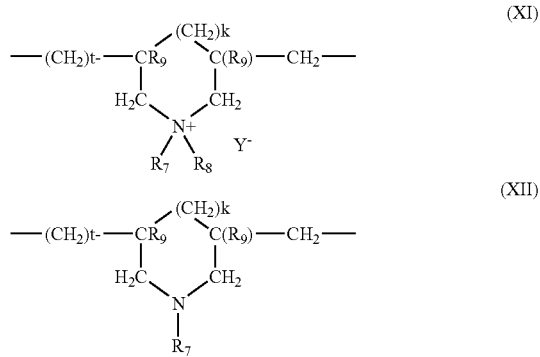

in which formulae k and t are equal to 0 or 1, the sum k+t being equal to 1; $R_9$ is chosen from a hydrogen atom and a methyl radical; $R_7$ and $R_8$, independently of each other, are chosen from alkyl groups having from 1 to 8 carbon atoms, such as from 1 to 4 carbon atoms; hydroxyalkyl groups in which the alkyl group may have, for example, 1 to 5 carbon atoms; and lower ($C_1$-$C_4$)amidoalkyl groups, or $R_7$ and $R_8$ may form, together with the nitrogen atom to which they are attached, heterocyclic groups such as piperidinyl or morpholinyl; $Y^-$ is an anion such as bromide, chloride, acetate, borate, citrate, tartrate, bisulphate, bisulphite, sulphate or phosphate. These polymers are described especially in French Patent 2,080,759 and in its certificate of addition 2,190,406.

Among the polymers defined above there may be mentioned as examples the dimethyldiallylammonium chloride homopolymer sold under the name "Merquat® 100" by the company Calgon (and its homologues of low weight-average molecular masses) and the copolymers of diallyl-dimethylammonium chloride and acrylamide marketed under the name "MERQUAT® 550".

(10) The quaternary diammonium polymer containing repeat units corresponding to the formula:

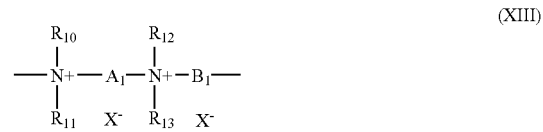

in which:

$R_{10}$, $R_{11}$, $R_{12}$ and $R_{13}$, which may be identical or different, are chosen from aliphatic, alicyclic and arylaliphatic radicals containing from 1 to 20 carbon atoms and from lower hydroxyalkyl aliphatic radicals, or else $R_{10}$, $R_{11}$, $R_{12}$ and $R_{13}$, together or separately, form, with the nitrogen atoms to which they are attached, heterocyclic rings optionally containing a second heteroatom other than nitrogen, or else $R_{10}$, $R_{11}$, $R_{12}$ and $R_{13}$ are chosen from linear and branched $C_1$-$C_6$ alkyl radicals substituted by a group chosen from nitrile, ester, acyl, amide and —CO—O—$R_{14}$-D or —CO—NH—$R_{14}$-D groups where $R_{14}$ is an alkylene and D a quaternary ammonium group;

$A_1$ and $B_1$ are chosen from polymethylene groups containing from 2 to 20 carbon atoms which may be linear or branched, saturated or unsaturated and which may contain, bonded to or inserted into the main chain, at least one aromatic ring, or at least one oxygen or sulphur atom or sulphoxide, sulphone, disulphide, amino, alkylamino, hydroxyl, quaternary ammonium, ureido, amide or ester groups, and $X^-$ is chosen from anions derived from an inorganic or organic acid;

A1, $R_{10}$ and $R_{12}$, with the two nitrogen atoms to which they are attached, may form a piperazine ring; in addition if A1 is a saturated or unsaturated, linear or branched alkylene or hydroxyalkylene radical, B1 may also be a group —$(CH_2)_n$—CO-D-OC—$(CH_2)_n$— in which n ranges from 1 to 100, such as from 1 to 50, and D denotes:

a) a glycol residue of formula: —O-Z-O—, where Z is chosen from linear and branched hydrocarbon radicals or a group corresponding to one of the following formulae:

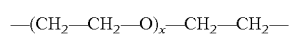

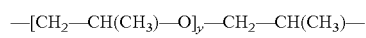

where x and y are chosen from integers ranging from 1 to 4, representing a defined and unique degree of polymerization or any number from 1 to 4 representing a mean degree of polymerization;

b) a disecondary diamine residue such as a piperazine derivative;
c) a diprimary diamine residue of formula: —NH—Y—NH—, where Y is a linear or branched hydrocarbon radical or else the divalent radica

—CH$_2$—CH$_2$—S—S—CH$_2$—CH$_2$—;

d) a ureylene group of formula: —NH—CO—NH—;

X$^-$ may be, for example, an anion such as chloride or bromide.

These polymers have a number-average molecular mass which generally ranges from 1000 to 100 000.

Polymers of this type are described, for instance, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use, for example, the polymers comprising repeating units corresponding to the following formula (XIV):

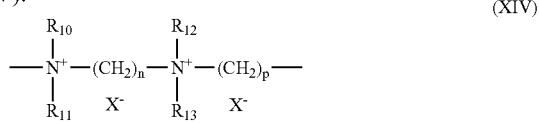

in which $R_{10}$, $R_{11}$, $R_{12}$ and $R_{13}$, which may be identical or different, are chosen from alkyl radicals having from 1 to 4 carbon atoms and from hydroxyalkyl radicals having from 1 to 4 carbon atoms, n and p are integers varying from 2 to 20 and X$^-$ is chosen from anions derived from an inorganic or organic acid.

(11) The quaternary polyammonium polymers comprising recurring units of formula (XV):

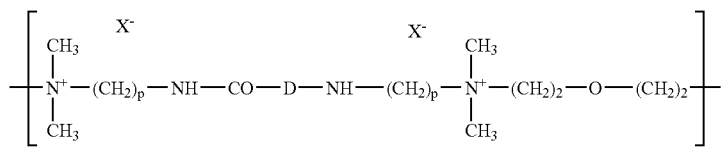

in which p is an integer varying from 1 to 6, D is zero or is chosen from a group —(CH$_2$)$_r$—CO— in which r is a number equal to 4 or to 7, X$^-$ is an anion.

Such polymers may be prepared according to the methods described in U.S. Pat. Nos. 4,157,388, 4,702,906, and 4,719,282. They are also described in Patent Application EP-A-122 324.

Among these, there may be mentioned for example the products "Mirapol® A 15", "Mirapol® AD1", "Mirapol® AZ1" and Mirapol® 175" sold by the company Miranol.

(12) Quaternary vinylpyrrolidone and vinylimidazole polymers such as, for example, the products marketed under the names Luviquat® FC 905, FC 550 and FC 370 by the company B.A.S.F.

(13) Polyamines like the Polyquart H sold by Henkel, referenced under the name of "Polyethylene Glycol (15) Tallow Polyamine" in the CTFA dictionary.

(14) The crosslinked polymers of methacryloyloxy(C$_1$-C$_4$ alkyl)tri(C$_1$-C$_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. For example, it is possible to employ a crosslinked acrylamide/methacryloyloxyethyltrimethylammonium chloride copolymer (20/80 by weight) in the form of a dispersion containing 50% by weight of said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed herein are polyalkyleneimines, such as polyethyleneimines, polymers containing vinylpyridine or vinylpyridinium units, condensates of polyamines and of epichlorohydrin, quaternary polyureylenes and chitin derivatives.

Among all the cationic polymers which may be used herein, the polymers of the families (1), (9), (10), (11) and (14) may be mentioned, and for example, the polymers with the recurring units of the following formulae (W) and (U):

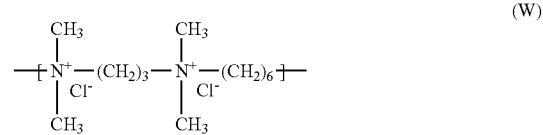

such as those whose molecular weight, determined by gel permeation chromatography, ranges from 9500 to 9900;

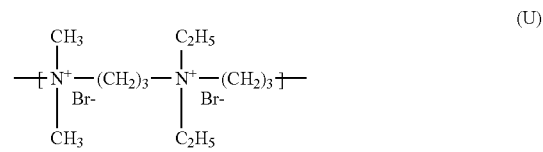

such as those whose molecular weight, determined by gel permeation chromatography, is about 1200.

The at least one additional cationic polymer may be present in the compositions disclosed herein in an amount ranging from 0.01 to 10% by weight relative to the total weight of the composition, for example, from 0.05 to 5%, such as from 0.1 to 3%.

Amphoteric Polymers

The at least one amphoteric polymer which can be used in accordance with the present invention may be chosen from the polymers containing K and M units distributed statistically in the polymer chain where K is a unit which is derived from a monomer containing at least one basic nitrogen atom and M is a unit which is derived from an acidic monomer containing at least one group chosen from carboxylic and sulphonic groups or alternatively K and M may be groups which are derived from zwitterionic monomers of carboxybetaines or of sulphobetaines;

K and M may also be chosen from cationic polymer chains containing primary, secondary, tertiary or quaternary amine groups, in which at least one of the amine groups carries a carboxylic or sulphonic group linked via a hydrocarbon radical or alternatively K and M form part of a chain of a polymer with an α,β-dicarboxylic ethylene unit in which one of the carboxylic groups has been caused to react with a polyamine containing one or more primary or secondary amine groups.

The amphoteric polymers corresponding to the definition given above which may be used include the following polymers:

1) The polymers resulting from the copolymerization of a monomer derived from a vinyl compound carrying a carboxylic group such as acrylic acid, methacrylic acid, maleic acid, alpha-chloroacrylic acid, and of a basic monomer derived from a substituted vinyl compound containing at least one basic atom such as dialkylaminoalkyl methacrylate and acrylate, dialkylaminoalkylmethacrylamide and acrylamide. Such compounds are described in U.S. Pat. No. 3,836,537. Mention may also be made of the sodium acrylate/acryamidopropyltrimethylammonium chloride copolymer sold under the name POLYQUART KE® 3033 by the company HENKEL.

The vinyl compound may also be a dialkyldiallylammonium salt such as dimethyldiallylammonium chloride. The copolymers of acrylic and of the latter monomer are offered under the names MERQUAT® 280, MERQUAT® 295 and MERQUAT® PLUS 3330 by the company CALGON.

(2) The polymers containing units which are derived from:
  a) at least one monomer chosen from acrylamides or methacrylamides substituted on the nitrogen by an alkyl radical,
  b) at least one acidic comonomer containing one or more reactive carboxylic groups, and
  c) at least one basic comonomer such as esters with primary, secondary, tertiary and quaternary amine substituents of acrylic and methacrylic acids and the product of quaternization of dimethylaminoethyl methacrylate with dimethyl or diethyl sulphate.

For example, the N-substituted acrylamides or methacrylamides may be groups whose alkyl radicals contain from 2 to 12 carbon atoms, such as N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers may be chosen from acrylic, methacrylic, crotonic, itaconic, maleic and fumaric acids as well as the alkyl monoesters having 1 to 4 carbon atoms of maleic or fumaric anhydrides or acids.

The basic comonomers may be chosen from methacrylates of aminoethyl, butylaminoethyl, N,N'-dimethylaminoethyl, and N-tert-butylaminoethyl.

For example, the copolymers whose CTFA name (4th ed. 1991) is Octylacrylamide/acrylates/butylaminoethylmethacrylate copolymer may be used, such as the products sold under the name AMPHOMER® or LOVOCRYL® 47 by the company NATIONAL STARCH.

(3) The partially or completely alkylated and crosslinked polyaminoamides derived from polyaminoamides of general formula:

 (XVI)

in which $R_{19}$ is chosen from divalent radicals derived from saturated dicarboxylic acids, mono- or dicarboxylic aliphatic acids with ethylenic double bond, esters of a lower alkanol having 1 to 6 carbon atoms of these acids or a radical which is derived from the addition of any one of said acids with a bis-primary or bis-secondary amine, and Z is chosen from radicals of bis-primary, mono- or bis-secondary polyalkylene-polyamines and may contain:

a) in a proportion of 60 to 100 mol %, the radical

 (XVII)

where x=2 and p=2 or 3, or alternatively x=3 and p=2 this radical being derived from the diethylenetriamine, triethylenetetraamine or dipropylenetriamine;

b) in a proportion of 0 to 40 mol %, the radical (XVII) above, in which x=2 and p=1 and which is derived from ethylenediamine, or the radical which is derived from piperazine:

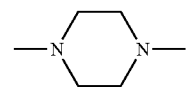

c) in a proportion of 0 to 20 mol %, the radical —NH—(CH$_2$)$_6$—NH— which is derived from hexamethylenediamine, these polyaminoamines being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyaminoamide and alkylated by the action of acrylic acid, chloroacetic acid or of an alkanesultone or of their salts.

The saturated carboxylic acids may, for example, be chosen from the acids having 6 to 10 carbon atoms such as adipic, 2,2,4-trimethyladipic and 2,4,4-trimethyladipic acid, terephthalic acid, the acids with an ethylene double bond such as for example acrylic, methacrylic and itaconic acids.

The alkanesultones used in the alkylation may be propane or butanesultone, and the salts of the alkylating agents may be the sodium or potassium salts.

4) The polymers containing zwitterionic units of formula:

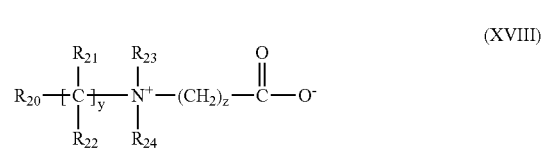 (XVIII)

in which $R_{20}$ is chosen from polymerizable unsaturated groups such as an acrylate, methacrylate, acrylamide or methacrylamide group, y and z are chosen from an integer from 1 to 3, $R_{21}$ and $R_{22}$ are chosen from a hydrogen atom, a methyl group, an ethyl group, or a propyl group, $R_{23}$ and $R_{24}$ are chosen from a hydrogen atom and an alkyl radical such that the sum of the carbon atoms in $R_{23}$ and $R_{24}$ does not exceed 10.

The polymers comprising such units may also comprise units derived from nonzwitterionic monomers such as dimethyl or diethylaminoethyl acrylate or methacrylate or alkyl acrylates or methacrylates, acrylamides or methacrylamides or vinyl acetate.

By way of example, there may be mentioned the copolymer of butyl methacrylate/dimethylcarboxymethylammonioethyl methacrylate such as the product sold under the name DIAFORMER Z301® by the company SANDOZ.

(5) The polymers derived from chitosan containing monomeric units corresponding to the following formulae (XIX), (XX), (XXI):

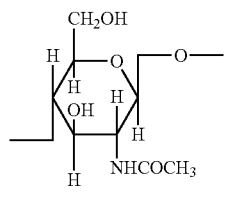

(XIX)

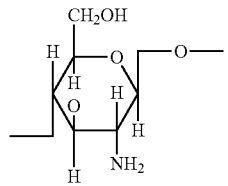

(XX)

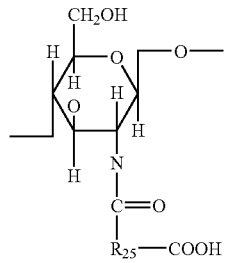

(XXI)

the (XIX) unit being present in proportions ranging from 0 to 30%, the (XX) unit in proportions ranging from 5 to 50% and the (XXI) unit in proportions ranging from 30 to 90%, it being understood that in this (XXI) unit, $R_{25}$ represents a radical of formula:

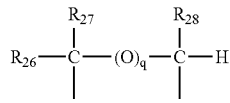

in which q is zero or 1;

if q=0, $R_{26}$, $R_{27}$ and $R_{28}$, which may be identical or different, are each chosen from a hydrogen atom, a methyl group, a hydroxyl group, an acetoxy group, an amino group, a monoalkylamine group, and a dialkylamine residue optionally interrupted by at least one nitrogen atom and/or optionally substituted with at least one group chosen from amine, hydroxyl, carboxyl, alkylthio and sulphonic groups, and an alkylthio residue whose alkyl group carries an amino residue, at least one of the $R_{26}$, $R_{27}$ and $R_{28}$ radicals being in this case a hydrogen atom;

or if q=1, $R_{26}$, $R_{27}$ and $R_{28}$ each are a hydrogen atom, as well as the acid-addition and base-addition salts formed by these compounds.

(6) The polymers derived from the N-carboxyalkylation of chitosan such as N-carboxymethyl chitosan or N-carboxybutyl chitosan sold under the name "EVALSAN®" by the company JAN DEKKER.

(7) The polymers corresponding to the general formula (XXII) as described for example in French Patent 1,400,366:

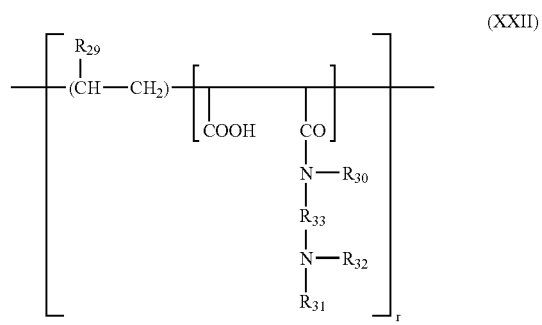

(XXII)

in which $R_{29}$ is chosen from a hydrogen atom, a $CH_3O$ radical, a $CH_3CH_2O$ radical, and a phenyl radical, $R_{30}$ is chosen from a hydrogen atom and lower alkyl radicals such as methyl or ethyl, $R_{31}$ is chosen from hydrogen and lower alkyl radicals such as methyl or ethyl, $R_{32}$ is chosen from lower alkyl radicals such as methyl or ethyl and a radical corresponding to the formula: $-R_{33}-N(R_{31})_2$, $R_{33}$ being chosen from a group $-CH_2-CH_2-$, $-CH_2-CH_2-CH_2-$ or $-CH_2-CH(CH_3)-$, $R_{31}$ having the meanings mentioned above, as well as the higher homologues of these radicals and containing up to 6 carbon atoms r is such that the molecular weight is from 500 to 6 000 000, for example, from 1000 to 1 000 000.

(8) Amphoteric polymers of the -D-X-D-X- type chosen from:

a) the polymers obtained by the action of chloroacetic acid or sodium chloroacetate on the compounds containing at least one unit of formula:

-D-X-D-X-D- (XXIII)

where D is a radical

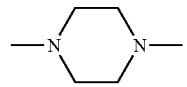

and X is the symbol E or E', E or E', which may be identical or different, are chosen from bivalent radicals which are alkylene radicals with linear or branched chains containing up to 7 carbon atoms in the principal chain which is unsubstituted or substituted with hydroxyl groups and which may contain, in addition, oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups;

b) The polymers of formula:

-D-X-D-X- (XXIV)

where D is a radical

and X is the symbol E or E' and, at least once, E'; E having the meaning indicated above and E' is a bivalent radical which is an alkylene radical with a linear or branched chain having up to 7 carbon atoms in the principal chain, which is unsubstituted or substituted with one or more hydroxyl radicals and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The copolymers $(C_1-C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

The at least one amphoteric polymer used herein, for example, may be those of the family (1).

The at least one amphoteric polymer may be present in an amount ranging from 0.01% to 10% by weight, such as from 0.05% to 5% by weight, and, for example, from 0.1% to 3% by weight, relative to the total weight of the composition.

The compositions disclosed herein may also comprise at least one surfactant other than the polyoxyalkylenated $C_{10}-C_{14}$ fatty alcohols. The surfactant(s) may be equally well chosen, alone or in the form of mixtures, from anionic, amphoteric, nonionic, zwitterionic and cationic surfactants.

The surfactants which are suitable for use herein include the following:

(i) Anionic Surfactant(s):

By way of example of anionic surfactants which can be used, alone or as mixtures, there may be mentioned, for example (nonlimiting list), the salts (such as alkali metal (for example sodium) salts, ammonium salts, amine salts, amino alcohol salts or magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamidesulphonates, alkyl aryl sulphonates, α-olefinsulphonates, paraffinsulphonates; $(C_6-C_{24})$alkyl sulphosuccinates, $(C_6-C_{24})$alkyl ether sulphosuccinates, $(C_6-C_{24})$alkylamide sulphosuccinates; $(C_6-C_{24})$alkyl sulphoacetates; $(C_6-C_{24})$ acyl sarcosinates and $(C_6-C_{24})$acyl glutamates. It is also possible to use $(C_6-C_{24})$alkyl polyglycoside carboxylic esters such as alkyl glucoside citrates, alkyl polyglycoside tartrate and alkyl polyglycoside sulphosuccinates, alkyl sulphosuccinamates; acyl isethionates and N-acyltaurates. The alkyl or acyl radical of all these various compounds may comprise, in one embodiment, from 12 to 20 carbon atoms, and the aryl radical may be chosen from phenyl and benzyl groups.

Also there may also be mentioned, as useful anionic surfactants, the salts of fatty acids such as the salts of oleic, ricinoleic, palmitic and stearic acids, the acids of copra oil or of hydrogenated copra oil; the acyllactylates whose acyl radical comprises 8 to 20 carbon atoms. It is also possible to use the alkyl D-galactoside uronic acids and their salts, the polyoxyalkylenated $(C_6-C_{24})$alkyl ether carboxylic acids, the polyoxyalkylenated $(C_6-C_{24})$alkylaryl ether carboxylic acids, the polyoxyalkylenated $(C_6-C_{24})$alkyl amido ether carboxylic acids and salts thereof, such as those comprising from 2 to 50 alkylene, e.g., ethylene, oxide groups, and mixtures thereof.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116-178) and, in the context of the presently claimed compositions, their nature does not assume any critical character. They can thus be chosen from (nonlimiting list) alpha-diols or polyethoxylated or polypropoxylated alkylphenols which have a fatty chain containing, for example, 8 to 18 carbon atoms, it being possible for the number of ethylene oxide or propylene oxide groups to range from 2 to 50. The copolymers of ethylene oxide and propylene oxide and the condensates of ethylene oxide and propylene oxide with fatty alcohols may also be mentioned; the polyethoxylated fatty amides containing, for example, from 2 to 30 mol of ethylene oxide, the polyglycerolated fatty amides containing on average 1 to 5 glycerol groups, such as 1.5 to 4; the oxyethylenated fatty acid esters of sorbitan containing from 2 to 30 mol of ethylene oxide; the fatty acid esters of sucrose, the fatty acid esters of polyethylene glycol, alkylpolyglycosides, the N-alkylglucamine derivatives, amine oxides such as the oxides of $(C_{10}-C_{14})$-alkylamines or the N-acylaminopropylmorpholine oxides.

(iii) Amphoteric or Zwitterionic Surfactant(s):

The amphoteric or zwitterionic surfactants, the nature of which is not of critical importance in the presently disclosed compositions, may be (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines may further be mentioned.

Among the amine derivatives, there may be mentioned the products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates having the respective structures:

$$R_2-CONHCH_2CH_2-N(R_3)(R_4)(CH_2COO^-)$$

in which: $R_2$ denotes an alkyl radical of an acid $R_2$—COOH present in hydrolysed copra oil, a heptyl, nonyl or undecyl radical, $R_3$ denotes a beta-hydroxyethyl group and $R_4$ a carboxymethyl group;

and $$R_2'-CONHCH_2CH_2-N(B)(C)$$

in which:

B is —CH$_2$CH$_2$OX', C is —(CH$_2$)$_z$—Y', with z=1 or 2,

X' is chosen from a —CH$_2$CH$_2$—COOH group and a hydrogen atom

Y' is chosen from —COOH and the radical —CH$_2$—CHOH—SO$_3$H

R$_2$' is chosen from an alkyl radical of an acid R$_9$—COOH present in copra oil or in hydrolysed linseed oil, an alkyl radical, such as C$_7$, C$_9$, C$_{11}$, or C$_{13}$, a C$_{17}$ alkyl radical and its iso form or an unsaturated C$_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Caprylamphodiacetate, Disodium Cocoamphodipropionate, Disodium Lauroamphodipropionate, Disodium Caprylamphodipropionate, Disodium Caprylamphodipropionate, Lauro-amphodipropionic acid, Cocoamphodipropionic acid.

By way of example, there may be mentioned the cocoamphodiacetate marketed under the trade name MIRANOL® C2M concentrated by the company RHODIA CHIMIE.

(iv) Cationic Surfactants:

Among the cationic surfactants useful herein, there may be mentioned (nonlimiting list): the salts of optionally polyoxyalkylenated primary, secondary or tertiary amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

The at least one surfactant may be present in the compositions disclosed herein in an amount by weight ranging from 0.01 to 40%, such as from 0.5 to 30% of the total weight of the composition.

Additional Thickening Agents

The compositions disclosed herein may also contain other rheology adjusting agents such as cellulosic thickeners (hydroxyethylcellulose, hydroxypropylcellulose, carboxymethylcellulose, and the like), guar gum and its derivatives (hydroxypropylguar and the like), gums of microbial origin (xanthan gum, scleroglucan gum, and the like), synthetic thickeners such as crosslinked homopolymers of acrylic acid and acrylamidopropanesulphonic acid and ionic or nonionic associative polymers such as the polymers marketed under the names PEMULEN® TR1 or TR2 by the company GOODRICH, SALCARE® SC90 by the company ALLIED COLLOIDS, ACULYN® 22, 28, 33, 44 or 46 by the company ROHM & HMS and ELFACOS® T210 and T212 by the company AKZO.

These supplementary thickeners may be present in an amount ranging from 0.01 to 10% by weight of the total weight of the composition.

The appropriate dyeing medium for the composition is, for example, an aqueous medium comprising water and optionally cosmetically acceptable organic solvents including alcohols such as ethyl alcohol, isopropyl alcohol, benzyl alcohol and phenylethyl alcohol, glycols or glycol ethers such as, for example, monomethyl, monoethyl and monobutyl ethers of ethylene glycol, propylene glycol or its ethers such as, for example, monomethyl ether of propylene glycol, butylene glycol, dipropylene glycol as well as the alkyl ethers of diethylene glycol such as for example monoethyl ether or monobutyl ether of diethylene glycol. The solvents may be present in concentrations ranging from 0.5 to 20% such as from 2 to 10% by weight relative to the total weight of the composition.

The composition A may also contain an effective quantity of other agents, moreover previously known in oxidation dyeing, such as various customary adjuvants such as sequestrants such as EDTA and etidronic acid, UV-screening agents, waxes, volatile or nonvolatile silicones which are cyclic or linear or branched, organomodified (for example with amine groups) or otherwise, preservatives, ceramides, pseudoceramides, vegetable, mineral or synthetic oils, vitamins or provitamins such as panthenol, opacifiers, associative polymers other than those of the present invention, for example, nonionic associative polyether-polyurethanes.

The composition may also contain at least one reducing agent and/or at least one antioxidant. These may be chosen from sodium sulphite, thioglycolic acid, thiolactic acid, sodium bisulphite, dehydroascorbic acid, hydroquinone, 2-methylhydroquinone, tert-butylhydroquinone and homogentisic acid, and be present in quantities ranging from 0.05 to 3% by weight relative to the total weight of the composition.

Of course persons skilled in the art will be careful to choose the possible additional compound(s) mentioned above so that the advantageous properties intrinsically attached to the dyeing composition according to the invention are not, or substantially not, impaired by the envisaged addition(s).

In the ready-to-use composition or in the composition B, the at least one oxidizing agent may be chosen from urea peroxide, alkali metal bromates or ferricyanides, persalts such as perborates and persulphates. For example, hydrogen peroxide may be used. In one embodiment, the at least one oxidizing agent is a solution of hydrogen peroxide whose titre may vary from 1 to 40 volumes, such as from 5 to 40.

It is also possible to use as oxidizing agent at least one oxidation-reduction enzyme such as laccases, peroxidases and oxidoreductases containing 2 electrons (such as uricase), where appropriate in the presence of their respective donor or cofactor.

The pH of the ready-to-use composition applied to the keratin fibers [composition resulting from the mixture of the dyeing composition A and of the oxidizing composition B and optionally of the composition C], may range from 4 to 11, such as from 6 to 10, and may be adjusted to the desired value by means of acidifying or alkalinizing agents well known in the state of the art for dyeing keratin fibers.

Among the alkalinizing agents, there may be mentioned by way of example aqueous ammonia, alkali metal carbonates, alkanolamines such as mono-, di- and triethanolamines as well their derivatives, oxyethylenated and/or oxypropylenated ethylenediamines and hydroxyalkylamines, sodium or potassium hydroxides and compounds having the following formula (XXV):

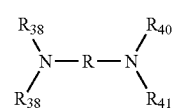

(XXV)

in which R is a propylene residue optionally substituted with a hydroxyl group or a C$_1$-C$_4$ alkyl radical; R$_{38}$, R$_{39}$, R$_{40}$ and $R_{41}$, which may be identical or different, are chosen from a hydrogen atom, $C_1$-$C_4$ alkyl radicals and $C_1$-$C_4$ hydroxyalkyl radicals.

The acidifying agents are conventionally, by way of example, chosen from inorganic and organic acids such as hydrochloric acid, orthophosphoric acid, carboxylic acids such as tartaric acid, citric acid, lactic acid or sulphonic acids.

The dyeing method according to the invention may comprise applying the ready-to-use composition, freshly prepared at the time of use from the compositions A and B and optionally C described above, to the dry or wet keratin fibers, and allowing it to act for an exposure time of, for example, from 1 to 60 minutes, such as from 10 to 45 minutes, rinsing the fibers, and optionally washing them with shampoo, and then rinsing them again, and drying them.

According to the disclosed methods, the compositions A and/or B may contain in addition at least one additional cationic or amphoteric polymer and at least one surfactant.

A concrete example illustrating the invention is indicated below, without however exhibiting a limiting character.

EXAMPLE

The following compositions were prepared:
(quantities expressed in grams)

Oxidizing Composition:

| | |
|---|---|
| Cetylstearyl alcohol (80%)/cetylstearyl alcohol containing 30 EO (20%) mixture (SINNOWAX AO from COGNIS) | 2.35 g |
| Oleic acid diethanolamine | 0.95 g |
| Glycerin | 0.5 g |
| Hydrogen peroxide as a 50% solution in water | 12 g |
| Sequestering agent | 0.15 g |
| Stabilizing agents | 0.125 g |
| Perfume | qs |
| Acidifying agents qs | pH 2.8 |
| Demineralized water qs | qs 100 g |

Dyeing Composition:

| | |
|---|---|
| Natural lauric acid | 2.5 g |
| Oxyethylenated lauryl alcohol (12 EO) | 7.5 g |
| Cetylstearyl alcohol (C16/C18 50/50) | 10 g |
| Glycol monostearate | 2 g |
| Oxyethylenated oleocetyl alcohol (30 EO) | 3 g |
| Oxyethylenated decyl alcohol (3 EO) | 10 g |
| Pyrogenic silica with a hydrophobic character | 1 g |
| Pure monoethanolamine | 1.2 g |
| Dimethyl diallyl ammmonium chloride homopolymer as a 40% aqueous solution | 7 g |
| Propylene glycol | 10 g |
| Terpolymer of vinylpyrrolidone, dimethyl aminopropylmethacrylamide and lauryldimethyl propylmethacrylamidoammonium chloride (74/15/11) | 4 g |
| Crosslinked polyacrylic acid | 0.4 g |
| Diethylenetriaminepentaacetic acid, pentasodium salt as a 40% aqueous solution | 2 g |
| Ammonium thiolactate as a 58% aqueous solution (50% as thiolactic acid) | 0.8 g |
| Mono-tert-butylhydroquinone | 0.3 g |
| 1,4-diaminobenzene | 0.24 g |
| 1-hydroxy-4-aminobenzene | 0.44 g |
| 1-hydroxy-2-aminobenzene | 0.028 g |
| 1,3-Dihydroxybenzene (resorcinol) | 0.192 g |
| 1-hydroxy-3-aminobenzene | 0.019 g |
| 1-methyl-2-hydroxy-4-betahydroxyethylaminobenzene | 0.021 g |
| 2-methyl-1, 3-dihydroxybenzene (2-methylresorcinol) | 0.055 g |
| Aqueous ammonia (at 20.5% of ammonia) | 10 g |
| Perfume | qs |
| Deionized water | qs 100 |

The polymer according to the disclosure was a vinylpyrrolidone/dimethylaminopropylmethacrylamide/lauryldimethylmethacrylamidoammonium chloride terpolymer provided by the company ISP under the reference POLYMER ACP-1 234.

The dyeing composition was mixed, at the time of use, in a plastic bowl and for 2 minutes, with the oxidizing composition given above, in an amount of 1 part of dyeing composition per 1.5 parts of oxidizing composition.

The mixture obtained was unctuous and was easy to prepare.

It was applied to natural grey hair which was 90% white and allowed to act for 30 minutes.

The product was easily removed by rinsing with water.

After washing with a standard shampoo, the hair was dried. It was dyed in a golden blond shade.

Comparative Example

A composition was prepared replacing the lauryl alcohol comprising 12 moles of EO and the decyl alcohol comprising 3 moles of EO by equivalent quantities of cetylstearyl alcohol comprising 3 and 12 moles of EO. The mixture obtained was less easy to prepare, less pleasant to apply and more difficult to remove. The shade obtained was of an inferior quality.

What is claimed is:

1. A composition for the oxidation dyeing of keratin fibers, comprising, in a suitable dyeing medium,
    at least one oxidation dye,
    at least one $C_{10}$-$C_{14}$ fatty alcohol and
    at least one cationic poly(vinyllactam) polymer comprising:
       a) at least one monomer chosen from vinyllactams and alkylvinyllactams;
       b) at least one monomer chosen from monomers of structures (Ia) or (Ib):

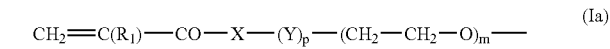
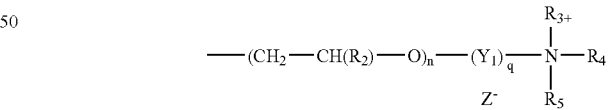
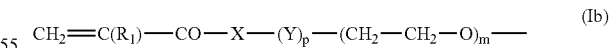
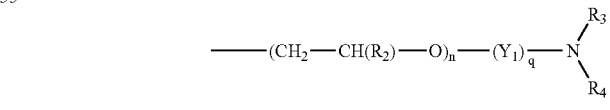

wherein:
    X is chosen from an oxygen atom and $NR_6$ radicals,
    $R_1$ and $R_6$, which may be identical or different, are chosen from hydrogen atoms, and linear and branched $C_1$-$C_5$ alkyl radicals,
    $R_2$ is chosen from linear and branched $C_1$-$C_4$ alkyl radicals, R$_3$, R$_4$ and R$_5$, which may be identical or different, are chosen from hydrogen atoms, linear and branched C$_1$-C$_{30}$ alkyl radicals, and radicals of formula (II):

$$-(Y_2')_r-(CH_2-CH(R_7)-O)_x-R_8 \quad (II)$$

wherein:

Y, Y$_1$ and Y$_2$, which may be identical or different, are chosen from linear and branched C$_2$-C$_{16}$ alkylene radicals, R$_7$ is chosen from hydrogen atoms, linear and branched C$_1$-C$_4$ alkyl radicals, and linear and branched C$_1$-C$_4$ hydroxyalkyl radical, R$_8$ is chosen from hydrogen atoms, linear and branched C$_1$-C$_{30}$ alkyl radicals, p, q and r, which may be identical or different, are integers equal to the value zero, or the value 1, m and n, which may be identical or different, are integers ranging from 0 to 100, x is an integer ranging from 1 to 100, Z is chosen from organic and inorganic acid anions, provided that:
  at least one of the substituents R$_3$, R$_4$, R$_5$ or R$_8$ is chosen from linear and branched C$_9$-C$_{30}$ alkyl radicals,
  if m or n is different from zero, then q is equal to 1,
  if m or n are equal to zero, then p or q is equal to 0; and
at least one synthetic thickener.

2. The composition according to claim 1, wherein the keratin fibers are hair.

3. The composition according to claim 1, wherein the at least one monomer chosen from vinyllactam and alkylvinyllactam monomers is a compound of formula (III):

$$CH(R_9)=C(R_{10})-N\underset{(CH_2)_s}{\diagup}\!\!=\!\!O \quad (III)$$

wherein:

s is an integer ranging from 3 to 6,

R$_9$ is chosen from hydrogen atoms and C$_1$-C$_5$ alkyl radicals,

R$_{10}$ is chosen from hydrogen atoms and C$_1$-C$_5$ alkyl radicals, provided that at least one of the radicals R$_9$ and R$_{10}$ is an hydrogen atom.

4. The composition according to claim 3, wherein the monomer of formula (III) is vinyl pyrrolidone.

5. The composition according to claim 1, wherein in formulae (Ia) or (Ib), the radicals R$_3$, R$_4$ and R$_5$, which may be identical or different, may be chosen from hydrogen atoms and linear and branched C$_1$-C$_{30}$ alkyl radicals.

6. The composition according to claim 1, wherein the monomer b) is a monomer of formula (Ia).

7. The composition according to claim 6, wherein in formula (Ia), m and n are equal to zero.

8. The composition according to claim 1, wherein the counterion Z$^-$ of the monomers of formula (Ia) is chosen from halide ions, phosphate ions, methosulphate ions, and tosylate ions.

9. The composition according to claim 1, further comprising at least one additional monomer chosen from cationic and nonionic monomers.

10. The composition according to claim 3, wherein the cationic poly(vinyllactam) is a terpolymer comprising:
  a) one monomer of formula (III),
  b) one monomer of formula (Ia), wherein
    p=1, q=0,
    R$_3$ and R$_4$, which may be identical or different, are chosen from hydrogen atoms and C$_1$-C$_5$ alkyl radicals, and
    R$_5$ is chosen from C$_9$-C$_{24}$ alkyl radicals, and
  c) one monomer of formula (Ib) wherein R$_3$ and R$_4$, which may be identical or different, are chosen from hydrogen atoms and C$_1$-C$_5$ alkyl radicals.

11. The composition according to claim 10, wherein the terpolymer comprises, by weight, 40 to 95% of monomer (a), 0.25 to 50% of monomer (b) and 0.1 to 55% of monomer (c).

12. The composition according to claim 1, wherein the cationic poly(vinyllactams) are chosen from the following terpolymers:
  vinylpyrrolidone/dimethylaminopropylmethacrylamide/dodecyldimethylmethacrylamidopropylammonium tosylate;
  vinylpyrrolidone/dimethylaminopropylmethacrylamide/cocoyldimethylmethacrylamidopropylammonium tosylate;
  vinylpyrrolidone/dimethylaminopropylmethacrylamide/lauryldimethylmethacrylamidopropylammonium tosylate, and
  vinylpyrrolidone/dimethylaminopropylmethacrylamide/lauryldimethylmethacrylamidopropylammonium chloride.

13. The composition according to claim 1, wherein the weight-average molecular mass of the cationic poly(vinyllactams) ranges from 500 to 20 000 000.

14. The composition according to claim 13, wherein the weight-average molecular mass of the cationic poly(vinyllactams) ranges from 200 000 to 2 000 000.

15. The composition according to claim 14, wherein the weight-average molecular mass of the cationic poly(vinyllactams) ranges from 400 000 to 800 000.

16. The composition according to claim 1, wherein the cationic poly(vinyllactam) and poly(vinyllactams) are present in the composition in an amount ranging from 0.01 to 10% by weight, relative to the total weight of the composition.

17. The composition according to claim 16, wherein the cationic poly(vinyllactam) and poly(vinyllactams) are present in the composition in an amount ranging from 0.1 to 5% by weight, relative to the total weight of the composition.

18. The composition according to claim 1, wherein the at least one C$_{10}$-C$_{14}$ fatty alcohol is present in the composition in an amount ranging from 0.1 to 40%, by weight, relative to the total weight of the composition.

19. The composition according to claim 18, wherein the at least one C$_{10}$-C$_{14}$ fatty alcohol is present in the composition in an amount ranging from 2 to 25%, by weight, relative to the total weight of the composition.

20. The composition according to claim 19, wherein the at least one C$_{10}$-C$_{14}$ fatty alcohol is present in the composition in an amount ranging from 5 to 20% by weight, relative to the total weight of the composition.

21. The composition according to claim 1, wherein the at least one oxidation dye is chosen from at least one oxidation base and at least one coupler and the acid addition salts thereof.

22. The composition according to claim 21, wherein the at least one oxidation dye is chosen from at least one oxidation base and the acid addition salts thereof.

23. The composition according to claim 21, wherein the at least one oxidation base is chosen from para-phenylenediamines, double bases, ortho-aminophenols, para-aminophenols, heterocyclic bases, and the acid addition salts thereof.

24. The composition according to claim 22, wherein the at least one oxidation base is present in an amount ranging from 0.0005 to 20% by weight, relative to the total weight of the composition.

25. The composition according to claim 21, wherein the at least one coupler is chosen from meta-phenylenediamines, meta-aminophenols, meta-diphenols, heterocyclic couplers, and the acid addition salts thereof.

26. The composition according to claim 21, wherein the at least one coupler is present in an amount ranging from 0.0001 to 20% by weight, relative to the total weight of the composition.

27. The composition according to claim 21, wherein the acid addition salts of the at least one oxidation dye are chosen from hydrochlorides, hydrobromides, tartrates, sulphates, lactates and acetates.

28. The composition according to claim 1, further comprising at least one direct dye.

29. The composition according to claim 1, further comprising at least one additional polymer chosen from at least one amphoteric polymer and at least one cationic polymer, provided that the cationic polymers are different from the at least one cationic poly(vinyllactam) polymer defined in claim 1.

30. The composition according to claim 29, wherein the at least one additional cationic polymer is a quaternary polyammonium polymer comprising recurring units corresponding to the formula (W):

$$-\!\!\!\left[\!\!\!\begin{array}{c}CH_3\\|\\N^+\!-\!(CH_2)_3\!-\!\\|\\Cl^-\\|\\CH_3\end{array}\!\!\!\begin{array}{c}CH_3\\|\\N^+\!-\!(CH_2)_6\\|\\Cl^-\\|\\CH_3\end{array}\!\!\!\right]\!\!\!- \quad (W)$$

31. The composition according to claim 29, wherein the at least one additional cationic polymer is a quaternary polyammonium polymer comprising recurring units corresponding to the formula (U):

$$-\!\!\!\left[\!\!\!\begin{array}{c}CH_3\\|\\N^+\!-\!(CH_2)_3\!-\!\\|\\Br^-\\|\\CH_3\end{array}\!\!\!\begin{array}{c}C_2H_5\\|\\N^+\!-\!(CH_2)_3\\|\\Br^-\\|\\C_2H_5\end{array}\!\!\!\right]\!\!\!- \quad (U)$$

32. The composition according to claim 29, wherein the at least one amphoteric polymer is a copolymer comprising as monomers at least acrylic acid and a salt of dimethyldiallylammonium.

33. The composition according to claim 29, wherein the at least one additional polymer is present in the composition in an amount ranging from 0.01% to 10%, by weight, relative to the total weight of the composition.

34. The composition according to claim 33, wherein the at least one additional polymer is present in the composition in an amount ranging from 0.05% to 5%, by weight, relative to the total weight of the composition.

35. The composition according to claim 34, wherein the at least one additional polymer is present in the composition in an amount ranging from 0.1% to 3% by weight, relative to the total weight of the composition.

36. The composition according to claim 1, further comprising at least one surfactant chosen from anionic, cationic, nonionic and amphoteric surfactants.

37. The composition according to claim 36, wherein the at least one surfactant is present in the composition in an amount ranging from 0.01 to 40% by weight, relative to the total weight of the composition.

38. The composition according to claim 37, wherein the at least one surfactant is present in the composition in an amount ranging from 0.5 to 30% by weight, relative to the total weight of the composition.

39. The composition according to claim 1, further comprising at least one additional thickening agent.

40. The composition according to claim 1, further comprising at least one reducing agent.

41. The composition according to claim 40, wherein the at least one reducing agent is present in the composition in an amount ranging from 0.05 to 3% by weight, relative to the total weight of the composition.

42. The composition according to claim 1, further comprising at least one oxidizing agent.

43. The composition according to claim 42, wherein the at least one oxidizing agent is chosen from hydrogen peroxide, urea peroxide, alkali metal bromates, ferricyanides, persalts, and oxidation-reduction enzymes that may optionally be used with their respective donor or cofactor.

44. The composition according to claim 43, wherein the at least one oxidizing agent is hydrogen peroxide.

45. The composition according to claim 44, wherein the at least one oxidizing agent is a hydrogen peroxide solution whose titre ranges from 1 to 40 volumes.

46. The composition according to claim 42, wherein it has a pH ranging from 4 to 11.

47. A process for dyeing keratin fibers, comprising applying to the fibers
 at least one composition A comprising, in an suitable dyeing medium, at least one oxidation dye,
 a composition B containing at least one oxidizing agent, which can develop the color at alkaline, neutral or acidic pH, and
 wherein composition A and composition B may be mixed just before application to the fibers, or applied sequentially without intermediate rinsing,
 and wherein at least one of compositions A and B further comprise at least one $C_{10}$-$C_{14}$ fatty alcohol, at least one synthetic thickener, and at least one cationic poly(vinyllactam) polymer comprising:
 a) at least one monomer chosen from vinyllactams and alkylvinyllactams; and
 b) at least one monomer chosen from monomers of structures (Ia) or (Ib):

$$CH_2\!=\!C(R_1)\!-\!CO\!-\!X\!-\!(Y)_p\!-\!(CH_2\!-\!CH_2\!-\!O)_m\!- \quad (Ia)$$

$$-\!(CH_2\!-\!CH(R_2)\!-\!O)_n\!-\!(Y_1)_{\overline{q}}\!\!\!\begin{array}{c}R_{3+}\\|\\N\!-\!R_4\\|\\R_5\end{array}$$
$$Z^-$$

$$CH_2\!=\!C(R_1)\!-\!CO\!-\!X\!-\!(Y)_p\!-\!(CH_2\!-\!CH_2\!-\!O)_m\!- \quad (Ib)$$

-continued

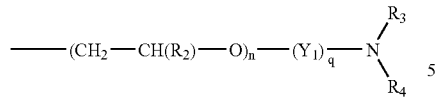

wherein:
X is chosen from an oxygen atom and $NR_6$ radicals,
$R_1$ and $R_6$, which may be identical or different, are chosen from hydrogen atoms, linear and branched $C_1$-$C_5$ alkyl radicals,
$R_2$ is chosen from linear and branched $C_1$-$C_4$ alkyl radicals,
$R_3$, $R_4$ and $R_5$, which may be identical or different, are chosen from hydrogen atoms, linear and branched $C_1$-$C_{30}$ alkyl radicals, and radicals of formula (II):

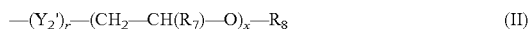 (II)

wherein:
Y, $Y_1$ and $Y_2$, which may be identical or different, are chosen from linear and branched $C_2$-$C_{16}$ alkylene radicals,
$R_7$ is chosen from hydrogen atoms, linear and branched $C_1$-$C_4$ alkyl radicals, and linear and branched $C_1$-$C_4$ hydroxyalkyl radical,
$R_8$ is chosen from hydrogen atoms, linear and branched $C_1$-$C_{30}$ alkyl radicals,
p, q and r, which may be identical or different, are integers equal to the value zero, or the value 1,
m and n, which may be identical or different, are integers ranging from 0 to 100,
x is an integer ranging from 1 to 100,
Z is chosen from organic and inorganic acid anions,
provided that:
at least one of the substituents $R_3$, $R_4$, $R_5$ or $R_8$ is chosen from linear and branched $C_9$-$C_{30}$ alkyl radicals,
if m or n is different from zero, then q is equal to 1,
if m or n are equal to zero, then p or q is equal to 0.

48. The process according to claim 47, wherein the human keratin fibers to be dyed are hair.

49. The process according to claim 47, further comprising
applying the ready-to-use composition, freshly prepared at the time of use from the compositions (A) and (B), to dry or wet keratin fibers,
allowing the composition to act for an exposure time ranging from 1 to 60 minutes,
rinsing the composition from the fibers,
optionally washing the fibers with shampoo,
optionally rinsing the fibers again, and
optionally drying the fibers.

50. The process according to claim 49, wherein the exposure time ranges from 10 to 45 minutes.

51. A two-compartment kit for dyeing keratin fibers, wherein
at least one compartment comprises at least one composition A1 comprising, in an appropriate dyeing medium, at least one oxidation dye, and
at least one other compartment comprises a composition B1 comprising, in a suitable dyeing medium, an oxidizing agent and at least one cationic poly(vinyllactam) polymer,
and wherein at least one of the compositions A1 and B1 further comprises at least one ted $C_{10}$-$C_{14}$ fatty alcohol, and at least one synthetic thickener, wherein said at least one cationic poly(vinyllactam) polymer comprises
a) at least one monomer chosen from vinyllactams and alkylvinyllactams; and
b) at least one monomer chosen from monomers of structure (Ia) or (Ib):

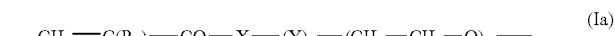 (Ia)

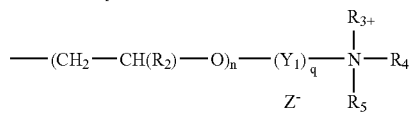

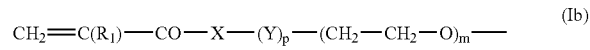 (Ib)

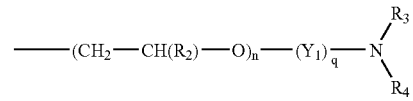

wherein:
X is chosen from an oxygen atom and $NR_6$ radicals,
$R_1$ and $R_6$, which may be identical or different, are chosen from hydrogen atoms, linear and branched $C_1$-$C_5$ alkyl radicals,
$R_2$ is chosen from linear and branched $C_1$-$C_4$ alkyl radicals,
$R_3$, $R_4$ and $R_5$, which may be identical or different, are chosen from hydrogen atoms, linear and branched $C_1$-$C_{30}$ alkyl radicals, and radicals of formula (II):

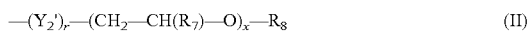 (II)

wherein:
Y, $Y_1$ and $Y_2$, which may be identical or different, are chosen from linear and branched $C_2$-$C_{16}$ alkylene radicals,
$R_7$ is chosen from hydrogen atoms, linear and branched $C_1$-$C_4$ alkyl radicals, and linear and branched $C_1$-$C_4$ hydroxyalkyl radical,
$R_8$ is chosen from hydrogen atoms, linear and branched $C_1$-$C_{30}$ alkyl radicals,
p, q and r, which may be identical or different, are integers equal to the value zero, or the value 1,
m and n, which may be identical or different, are integers ranging from 0 to 100,
x is an integer ranging from 1 to 100,
Z is chosen from organic and inorganic acid anions,
provided that:
at least one of the substituents $R_3$, $R_4$, $R_5$ or $R_8$ is chosen from linear and branched $C_9$-$C_{30}$ alkyl radicals,
if m or n is different from zero, then q is equal to 1, and
if m or n are equal to zero, then p or q is equal to 0.

52. The two-compartment kit for dyeing keratin fibers according to claim 51, wherein the keratin fibers are hair.

53. A multi-compartment kit for dyeing keratin fibers wherein
at least one first compartment comprises a composition A2 comprising, in a suitable dyeing medium, at least one oxidation dye, and optionally at least one $C_{10}$-$C_{14}$ fatty alcohol;
at least one second compartment comprising a composition B2 comprising, in a suitable dyeing medium, at least one oxidizing agent, and optionally at least one $C_{10}$-$C_{14}$ fatty alcohol;

at least one third compartment comprising a composition $C_2$ comprising, in a suitable dyeing medium, at least one cationic poly(vinyllactam) polymer comprising:
 a) at least one monomer chosen from vinyllactams and alkylvinyllactams;
 b) at least one monomer chosen from monomers of structures (Ia) or (Ib):

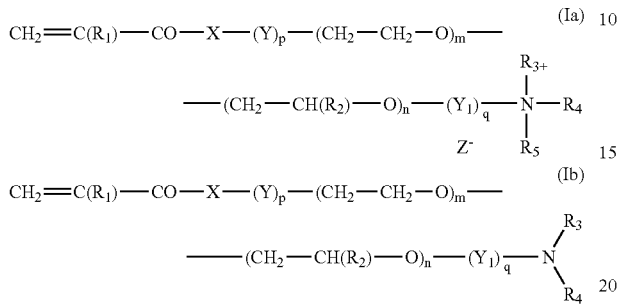

wherein:
 X is chosen from an oxygen atom and $NR_6$ radicals,
 $R_1$ and $R_6$, which may be identical or different, are chosen from hydrogen atoms, linear and branched $C_1$-$C_5$ alkyl radicals,
 $R_2$ is chosen from linear and branched $C_1$-$C_4$ alkyl radicals,
 $R_3$, $R_4$ and $R_5$, which may be identical or different, are chosen from hydrogen atoms, linear and branched $C_1$-$C_{30}$ alkyl radicals, and radicals of formula (II):

$$-(Y_2')_r-(CH_2-CH(R_7)-O)_x-R_8 \qquad (II)$$

wherein:
 Y, $Y_1$ and $Y_2$, which may be identical or different, are chosen from linear and branched $C_2$-$C_{16}$ alkylene radicals,
 $R_7$ is chosen from hydrogen atoms, linear and branched $C_1$-$C_4$ alkyl radicals, and linear and branched $C_1$-$C_4$ hydroxyalkyl radicals,
 $R_8$ is chosen from hydrogen atoms, linear and branched $C_1$-$C_{30}$ alkyl radicals,
 p, q and r, which may be identical or different, are integers equal to the value zero, or the value 1,
 m and n, which may be identical or different, are integers ranging from 0 to 100,
 x is an integer ranging from 1 to 100,
 Z is chosen from organic and inorganic acid anions,
 provided that:
  at least one of the substituents $R_3$, $R_4$, $R_5$ or $R_8$ is chosen from linear and branched $C_9$-$C_{30}$ alkyl radicals,
  if m or n is different from zero, then q is equal to 1, and if m or n are equal to zero, then p or q is equal to 0;
 wherein at least one of the compositions A2, B2, and $C_2$ further comprises at least one synthetic thickener.

54. The composition according to claim 1, wherein the $C_{10}$-$C_{14}$ fatty alcohol is a nonpolyoxyalkylenated fatty alcohol.

55. The composition according to claim 1, wherein the $C_{10}$-$C_{14}$ fatty alcohol is a polyoxyalkylenated fatty alcohol.

56. The composition according to claim 55, wherein the $C_{10}$-$C_{14}$ fatty alcohol is a polyoxyethylenated fatty alcohol comprising from 2 to 20 oxyethylene (EO) units.

57. The composition according to claim 56, wherein the $C_{10}$-$C_{14}$ fatty alcohol is a polyoxyethylenated fatty alcohol comprising from 3 to 15 oxyethylene (EO) units.

58. The composition according to claim 57, wherein the $C_{10}$-$C_{14}$ fatty alcohol is oxyethylenated 12 EO lauryl alcohol.

59. The composition according to claim 57, wherein the $C_{10}$-$C_{14}$ fatty alcohol is oxyethylenated 3 EO capryl alcohol.

* * * * *

UNITED STATES PATENT AND TRADEMARK OFFICE
CERTIFICATE OF CORRECTION

| | | |
|---|---|---|
| PATENT NO. | : 7,323,015 B2 | Page 1 of 1 |
| APPLICATION NO. | : 10/688970 | |
| DATED | : January 29, 2008 | |
| INVENTOR(S) | : François Cottard et al. | |

It is certified that error appears in the above-identified patent and that said Letters Patent is hereby corrected as shown below:

In claim 1, column 27, line 4, "—$(Y_2')_r$—$(CH_2$—$CH(R_7)$—$O)_x$—$R_8$" should read -- —$(Y_2)_r$—$(CH_2$—$CH(R_7)$—$O)_x$—$R_8$--.

In claim 4, column 27, line 49, "vinyl pyrrolidone." should read --vinylpyrrolidone.--.

In claim 47, column 31, line 18, "—$(Y_2')_r$—$(CH_2$—$CH(R_7)$—$O)_x$—$R_8$" should read -- —$(Y_2)_r$—$(CH_2$—$CH(R_7)$—$O)_x$—$R_8$--.

In claim 51, column 31, line 66, "one ted $C_{10}$-$C_{14}$" should read --one $C_{10}$-$C_{14}$--.

In claim 51, column 32, line 32, "—$(Y_2')_r$—$(CH_2$—$CH(R_7)$—$O)_x$—$R_8$" should read -- —$(Y_2)_r$—$(CH_2$—$CH(R_7)$—$O)_x$—$R_8$--.

In claim 53, column 33, line 2, "$C_2$" should read --C2--.

In claim 53, column 33, line 33, "—$(Y_2')_r$—$(CH_2$—$CH(R_7)$—$O)_x$—$R_8$" should read -- —$(Y_2)_r$—$(CH_2$—$CH(R_7)$—$O)_x$—$R_8$--.

In claim 53, column 34, line 18, "$C_2$" should read --C2--.

Signed and Sealed this

Tenth Day of June, 2008

JON W. DUDAS
*Director of the United States Patent and Trademark Office*